United States Patent [19]

Kiehs et al.

[11] 4,083,971

[45] Apr. 11, 1978

[54] PYRIDYLPHOSPHORIC ACID DERIVATIVES

[75] Inventors: Karl Kiehs, Lampertheim; Heinrich Adolphi; Hans Theobald, both of Limburgerhof, all of Germany

[73] Assignee: BASF Aktiengesellschaft, Ludwigshafen, Germany

[21] Appl. No.: 765,930

[22] Filed: Feb. 7, 1977

[30] Foreign Application Priority Data

Mar. 6, 1976 Germany ............................ 2609312

[51] Int. Cl.$^2$ ...................... A01N 9/22; C07D 213/55

[52] U.S. Cl. ............................ 424/200; 260/294.8 K; 260/295.5 R

[58] Field of Search .................... 260/294.8 K, 297 P, 260/295.5 R; 424/200

[56] References Cited

U.S. PATENT DOCUMENTS

| | | | |
|---|---|---|---|
| 3,244,586 | 4/1966 | Rigterink ...................... | 260/294.8 K |
| 3,635,987 | 1/1972 | Riehen et al. ................ | 260/294.8 K |

*Primary Examiner*—Alan L. Rotman
*Attorney, Agent, or Firm*—Keil, Thompson & Shurtleff

[57] ABSTRACT

New pyridylphosphoric acid derivatives, a process for the manufacture thereof by reaction of pyridinecarboxylic acid esters with salts of phosphoric acid derivatives, and pesticides containing these new pyridylphosphoric acid derivatives as active ingredients. The compounds of the invention have the formula

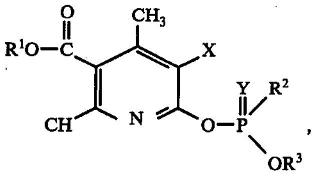

where X denotes hydrogen or halogen, Y denotes oxygen or sulfur, $R^1$ denotes linear or branched alkyl, alkenyl or alkynyl of a maximum of 6 carbons atoms, or unsubstituted or halogen-substituted phenyl or benzyl, $R^2$ denotes linear or branched alkyl, unsubstituted phenyl, substituted phenyl, alkyloxy or alkylthio of a maximum of 6 carbon atoms, alkenyloxy or alkenylthio of a maximum of 6 carbon atoms, alkynyloxy or alkynylthio of a maximum of 6 carbon atoms, amino or alkylamino with from 1 to 4 carbon atoms in the alkyl moiety, or dialkylamino with from 1 to 4 carbons atoms per alkyl moiety, and $R^3$ denotes alkyl of from 1 to 4 carbon atoms.

6 Claims, No Drawings

PYRIDYLPHOSPHORIC ACID DERIVATIVES

The present invention relates to new pyridylphosphoric acid derivatives, a process for their manufacture, and pesticides containing these phosphoric acid derivatives as active ingredients.

It is known (German Pat. No. 1,445,659) that pyridylphosphorus compounds bearing halogen atoms on the pyridyl radical have an insecticidal action. However, the persistence of these active ingredients is unsatisfactory for combatting for instance flies, fruit flies and caterpillars.

The new pyridylphosphoric acid derivatives have the formula I

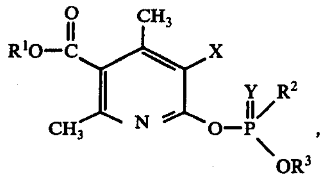

where X denotes hydrogen or halogen, Y denotes oxygen or sulfur, $R^1$ denotes linear or branched alkyl, alkenyl or alkynyl or a maximum of 6 carbon atoms, or unsubstituted or halogen-substituted phenyl or benzyl, $R^2$ denotes linear or branched alkyl, unsubstituted phenyl, substituted phenyl, alkyloxy or alkylthio of a maximum of 6 carbon atoms, alkenyloxy or alkenylthio of a maximum of 6 carbon atoms, alkynyloxy or alkynylthio of a maximum of 6 carbon atoms, amino or alkylamino with from 1 to 4 carbon atoms in the alkyl moiety, or dialkylamino with from 1 to 4 carbon atoms per alkyl moiety, and $R^3$ denotes alkyl of from 1 to 4 carbon atoms.

Examples of substituents for $R^1$ are the alkyl groups methyl, ethyl, n-propyl, isopropyl, butyl, pentyl and hexyl, the alkenyl groups allyl, butenyl, pentenyl and hexenyl, the alkynyl groups propargyl, butynyl, isobutynyl, pentynyl and hexynyl, and phenyl, p-chlorophenyl, o-chlorophenyl, m-chlorophenyl, 3,4-dichlorophenyl, 3,5-dichlorophenyl, 2,4-dichlorophenyl, 2,4,5-trichlorophenyl, benzyl, p-chlorobenzyl, 3,4-dichlorobenzyl, and 2,4,5-trichlorobenzyl.

Alkyl groups which $R^2$ may denote are methyl, ethyl, n-propyl, isopropyl, butyl, pentyl and hexyl; alkyloxy, alkenyloxy and alkynyloxy which $R^2$ may denote are methoxy, ethoxy, n-propoxy, isopropoxy, n-butoxy, isobutoxy, hexoxy, propenoxy, butenoxy, hexenoxy, propyn-(2)-oxy, butynoxy, isobutynoxy, and hexynoxy; alkylthio, alkenylthio and alkynylthio groups which $R^2$ may denote are methylthio, ethylthio, n-propylthio, isopropylthio, n-butylthio, isobutylthio, hexylthio, propenylthio, butenethio, e.g., butene-(2)-thio, hexerethio, propyne-(2)-thio, butynethio, isobutynethio, pentynethio and hexynethio. $R^2$ may also denote an amine group, an alkylamino group, e.g., methylamino, ethylamino, n-propylamino, isopropylamino, tert.-butylamino, n-butylamino and sec-butylamino, or a dialkylamino group, e.g., dimethylamino, diethylamino, di-n-propylamino, diisopropylamino, di-n-butylamino, di-sec-butylamino, and methylethylamino.

Suitable alkyl radicals for $R^3$ are methyl, ethyl, n-propyl, isopropyl and butyl.

Any halogen, i.e., fluorine, chlorine, bromine and iodine, may be used for X, chlorine and bromine being preferred.

The pyridylphosphoric acid derivatives of the invention of the formula I have a better insecticidal and acaricidal action than prior art compounds having an analogous constitution and scope of action. An outstanding feature is their excellent persistence.

The new phosphoric acid derivatives may be prepared by reaction of 6-hydroxy-2,4-dimethylpyridine carboxylic acid esters-(3) of the formula

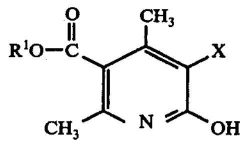

II with a phosphoric acid derivative of the formula

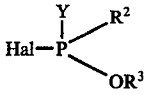

III.

The symbols $R^1$, $R^2$, $R^3$, X and Y in formulae II and III have the above meanings. Hal denotes halogen, especially chlorine and bromine.

The reaction is preferably carried out in solvents or diluents inert to the reactants. Particularly suitable examples are ethers such as dioxane and tetrahydrofuran, ketones such as acetone, methyl ethyl ketone and diethyl ketone, nitriles such as acetonitrile and propionitrile, chlorinated aliphatic hydrocarbons such as dichloromethane, 1,1-dichloroethane and 1,2-dichloroethane, aromatic hydrocarbons such as benzene, toluene, xylenes and chlorobenzenes, dimethylformamide and dimethyl sulfoxide.

The hydrogen halide evolved during the reaction may be removed from the mixture by passing in inert gas, e.g., nitrogen, or by binding it with an acid acceptor. Any conventional acid-binding agent may be used for this purpose. The following compounds are particularly suitable: alkali carbonates, alkali bicarbonates, e.g., sodium carbonate, alkali alcoholates, e.g., sodium and potassium ethylate and sodium and potassium methylate, aliphatic, aromatic and heterocyclic amines, e.g., trimethylamine, triethylamine, dimethylaniline, dimethylbenzylamine and pyridine.

In some cases, for instance when sterically hindered compounds of formulae II or III are used, it is advisable, in order to increase the conversion, to prepare the alkali metal salts of compounds of formula II first, and then to react them with the phosphoric acid derivatives of the formula III.

The two reactants may be used in equimolar amounts, or either in excess.

Reaction temperatures are from 0° to 150° C, preferably 50° to 90° C.

The pyridine derivatives of the formula II used as starting compounds may be obtained in conventional manner by reaction of isodehydroacetic acid esters of the formula IV with ammonia (Ann. Chem., 259, 173–186, 1890):

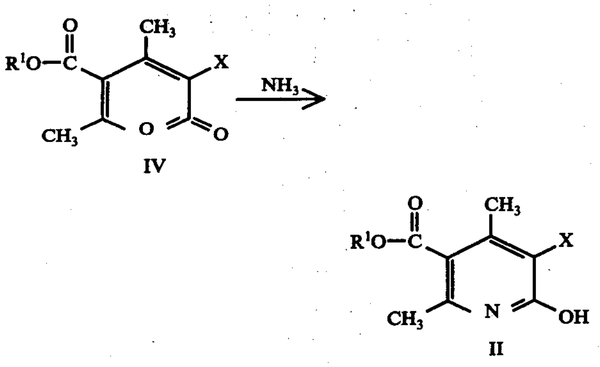

IV

II

The substituents $R^1$ and X have the above meanings.

To obtain the pyridine derivatives of the formula II, the isodehydroacetic acid esters of the formula IV are, as is known from the literature, gassed with ammonia, without a solvent, first at 20° C and then at 150° C to complete the reaction. The product obtained is taken up in methanol and the pyridine derivatives of the formula II are precipitated with ether or petroleum ether.

The new compounds are obtained as oils which usually cannot be distilled without decomposition occurring; however, "incipient distillation", i.e., heating for a fairly long period of time at moderately elevated temperatures and subatmospheric pressure, removes the residual volatiles and enables the compounds to be purified in this way. NMR spectra are used to identify the compounds.

The following examples illustrate the preparation of the new phosphoric acid derivatives. In the examples, parts by weight bear the same relation to parts by volume as kilograms to liters.

1.

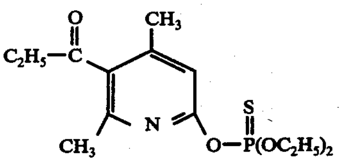

18 parts by weight of sodium methylate (30% solution in methanol) is added to 19.5 parts by weight of 2-hydroxy-4,6-di-methylpyridinecarboxylic acid ethyl ester-(3) in 150 parts by volume of methanol, and the mixture stirred for 1 hour at 60° C. The solvent is then removed, the residue is taken up in 100 parts by volume of acetonitrile, and 18.9 parts by weight of diethoxythiophosphoryl chloride is added. The mixture is stirred for 5 hours at 70° C and then cooled, the precipitate is filtered off and the filtrate concentrated. The oil which remains is taken up in toluene and treated with 2% aqueous sodium bicarbonate solution. The organic phase is dried over sodium sulfate, concentrated and subjected to incipient distillation at 60° C. There is obtained 32 parts by weight (92% of theory) of a pale yellow oil.

$C_{14}H_{22}NPO_5S$ (347)

| | C | H | N | P | S |
|---|---|---|---|---|---|
| Calc.: | 48.5 | 6.3 | 4.0 | 8.9 | 9.2 |
| Found: | 47.8 | 6.6 | 4.3 | 9.3 | 9.2 |

100 MHz nmr spectrum in $CDCl_3$ (δ values): 1.38 (9H); 2.32 (3H); 2.5 (3H); 4.15–4.58 (6H); 6.77 (1H).

2.

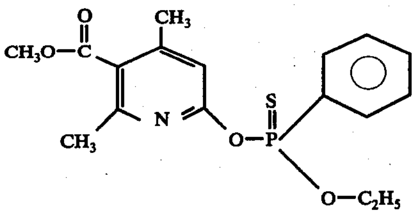

17.6 parts by weight of phenylthiophosphonic acid ethyl ester chloride is added to 14.5 parts by weight of 2-hydroxy-4,6-dimethylpyridinecarboxylic acid methyl ester-(3) in 150 parts by volume of acetonitrile; the mixture is stirred for 6 hours at 60° to 70° C while passing in dry nitrogen. The solvent is then removed, the oil which remains is taken up in toluene and treated with 2% aqueous sodium bicarbonate solution. The organic phase is dried over sodium sulfate, filtered and concentrated. Incipient distillation at 60° C/0.1 mm Hg gives 24.8 parts by weight (85% of theory) of a pale yellow oil.

$C_{17}H_{20}NPO_4S$ (365)

| | C | H | N | S | P |
|---|---|---|---|---|---|
| Calc.: | 55.9 | 5.5 | 3.8 | 8.8 | 8.5 |
| Found: | 55.5 | 5.7 | 4.0 | 9.5 | 9.2 |

60 MHz nmr spectrum (δ values): 1.3 (3H); 2.18 (3H); 2.43 (3H); 3.8 (3H); 4.05–4.67 (2H); 5.5 (1H); 7.16–7.6 (3H); 7.7–8.2 (2H).

3.

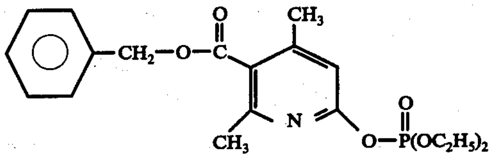

10.9 parts by weight of 2-hydroxy-4,6-dimethylpyridinecarboxylic acid benzyl ester-(3), 10 parts by weight of finely powdered sodium carbonate and 7.35 parts by weight of diethoxythiophosphoryl chloride are stirred for 7 hours at 60° C. After the mixture has cooled, the precipitate is filtered off and the filtrate is concentrated. The residue is stirred with toluene and washed with 2% aqueous sodium bicarbonate solution. The organic phase is dried over sodium sulfate, filtered, concentrated, and subjected to incipient distillation at 60° C/0.1 mm Hg. There is obtained 11.7 parts by weight (70% of theory) of a yellow oil.

$C_{19}H_{24}NPO_6$ (393)

| | C | H | N | P |
|---|---|---|---|---|
| Calc.: | 58.0 | 6.1 | 3.6 | 7.9 |
| Found: | 57.6 | 6.6 | 3.8 | 7.7 |

220 MHz nmr spectrum (δ values): 1.47 (6H); 2.28 (3H); 2.55 (3H); 4.3–4.55 (4H); 5.5 (2H); 6.92 (1H); 7.38–7.52 (5H).

The following compounds are obtained analogously:

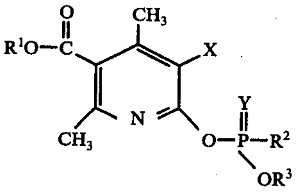

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

| No. | $R^1$ | $R^2$ | $R^3$ | X | Y | MHz nmr spectrum; δvalues |
|---|---|---|---|---|---|---|
| 4 | $CH_3$ | $OC_2H_5$ | $C_2H_5$ | H | S | 60 MHz: 1.32 (6H); 2.3 (3H); 2.46 (3H); 3.87 (3H); 3.75–4.64 (4H); 6.72 (1H). |
| 5 | $CH_3$ | $OC_2H_5$ | $C_2H_5$ | Br | S | 60 MHz: 1.28 (6H); 2.33 (3H); 2.5 (3H); 3.9 (3H); 3.73–4.73 (4H). |
| 6 | $CH_3$ | S-i-$C_3H_7$ | $C_2H_5$ | H | S | |
| 7 | $CH_3$ | $OC_2H_5$ | $C_2H_5$ | H | 0 | |
| 8 | $CH_3$ | $NHCH_3$ | $C_2H_5$ | H | S | |
| 9 | $C_2H_5$ | $OC_2H_5$ | $C_2H_5$ | Cl | S | 100 MHz: 1.28–1.49 (9H); 2.35 (3H); 2.52 (3H); 4.13–4.61 (6H). |
| 10 | $C_2H_5$ | $OC_2H_5$ | $CH_3$ | Cl | S | |
| 11 | $C_2H_5$ | S-n-$C_3H_7$ | $C_2H_5$ | H | 0 | |
| 12 | $C_2H_5$ | NH(i$C_3H_7$) | $CH_3$ | H | 0 | |
| 13 | $C_2H_5$ | S-n-$C_3H_7$ | $C_2H_5$ | Cl | 0 | |
| 14 | $C_2H_5$ | $CH_3$ | $C_2H_5$ | H | S | |
| 15 | $C_2H_5$ | $CH_3$ | n-$C_3H_7$ | H | S | |
| 16 | $C_2H_5$ | $OC_2H_5$ | $C_2H_5$ | Br | S | 60 MHz: 1.15–1.6 (9H); 2.28–2.33 (6H); 4.2–4.6 (6H). |
| 17 | $C_2H_6$ | $N(CH_3)_2$ | $C_2H_5$ | H | S | |
| 18 | $C_2H_5$ | S-n-$C_3H_7$ | $C_2H_5$ | Br | S | 60 MHz: 1.02 (3H); 1.2–1.6 (6H); 1.73 (2H); 2.45 (6H); 2.8–3.3 (2H); 4.33 (2H); 4.44 (2H). |
| 19 | $C_2H_5$ | S-n-$C_3H_7$ | $C_2H_5$ | H | S | 60 MHz: 1.00 (3H); 1.17–1.6 (6H); 1.75 (2H); 2.32 (3H); 2.50 (3H); 2.75 (3H); 2.75–3.3 (2H); 4.0–4.5 (4H); 6.83 (1H). |
| 20 | 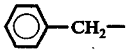 | $OC_2H_5$ | $C_2H_5$ | H | S | 220 MHz: 1.48 (6H); 2.43 (3H); 2.57 (3H); 4.37–4.6 (4H); 5.53 (2H); 6.91 (1H); 7.45–7.72 (5H). |
| 21 | 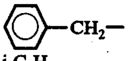 | 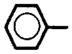 | $C_2H_5$ | H | S | 220 MHz: 1.47 (3H); 2.34 (3H); 2.5 (3H); 4.42–4.68 (2H); 4.49 (2H); 6.81 (1H); 7.33–7.82 (8H); 7.96–8.4 (2H). |
| 22 | i-$C_3H_7$ | $OC_2H_5$ | $C_2H_5$ | H | S | |
| 23 | i-$C_3H_7$ | n-$C_3H_7$—S | $C_2H_5$ | H | 0 | |
| 24 | $C_2H_5$ | n-$C_4H_9$S | $CH_3$ | H | 0 | |
| 25 | $C_2H_5$ | n-$C_4H_9$S | $CH_3$ | Cl | 0 | |
| 26 | $CH_2$=CH—$CH_2$ | $OC_2H_5$ | $C_2H_5$ | H | S | |
| 27 | HC≡C—$CH_2$— | n-$C_3H_7$S | $C_2H_5$ | H | S | |
| 28 | HC≡C—CH($CH_3$)— | $C_2H_5$—O | $C_2H_5$ | HS | | |
| 29 | i-$C_3H_7$ | NH(i-$C_3H_7$) | $C_2H_5$ | Cl | 0 | |
| 30 | i-$C_3H_7$ | $N(CH_3)_2$ | $CH_3$ | H | 0 | |
| 31 | i-$C_3H_7$ | $NHCH_3$ | $C_2H_5$ | Br | 0 | |
| 32 | 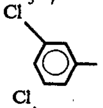 | $C_2H_5O$ | $C_2H_5$ | H | S | |
| 33 | 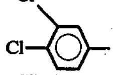 | NH(i-$C_3H_7$) | $C_2H_5$ | Cl | 0 | |
| 34 | 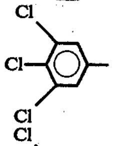 | $N(CH_3)_2$ | $C_2H_5$ | H | 0 | |
| 35 | 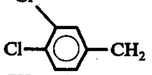 | NH(i-$C_3H_7$) | $C_2H_5$ | H | 0 | |
| 36 | $CH_3$—$CH_2$— | CH($CH_3$)— | $C_2H_5O$ | $C_2H_5$Cl | S | |
| 37 | $C_2H_5$ | n-$C_3H_7$I | n-$C_3H_7$ | Br | S | |
| 38 | $CH_3$ | n-$C_3H_7$O | O | n-$C_3H_7$ | 0 | |
| 39 | $CH_3$ | $CH_3$ | $C_2H_5$ | H | S | |
| 40 | $CH_3$ | $C_2H_5$ | $C_2H_5$ | Cl | S | |
| 41 | $C_2H_5$ | $CH_3$ | $CH_3$ | H | S | |
| 42 | $C_2H_5$ | $C_2H_5$ | $C_2H_5$ | Br | S | |
| 43 | i-$C_3H_7$ | $CH_3$ | $C_2H_5$ | H | S | |
| 44 | i-$C_3H_7$ | $CH_3$ | $C_2H_5$ | H | S | |

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenosulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredients may also be successfully used in the ultra-low volume method, where it is possible to apply formulations containing more than 95% of active ingredient.

There may be added to the individual active ingredients (if desired, immediately before use (tankmix)) oils of various types, herbicides, fungicides, insecticides and bactericides.

These agents may be added to the compounds according to the invention in a ratio by weight of from 1:10 to 10:1.

Formulations of the active ingredients are described in the following examples.

EXAMPLE A 20 parts by weight of O,O-diethyl-O-[4,6-dimethyl-5-carboxyethylpyridin-(2)-yl]-thiophosphate is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE B 20 parts by weight of O,O-diethyl-O-[4,6-dimethyl-5-carboxybenzylpyridin-(2)-yl]-thiophosphate is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE C 20 parts by weight of O,O-diethyl-O-[4,6-dimethyl-3-bromo-5-carboxyethylpyridin-(2)-yl]-thiophosphate is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE D 30 parts by weight of O,O-diethyl-O-[4,6-dimethyl-5-carboxymethylpyridin-(2)-yl]-thiophosphate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

The active ingredients according to the invention may be used for combatting pests such as sucking and biting insects, Diptera and mites.

The main representatives of the sucking insects are aphids (Aphidae) such as *Myzus persicae, Doralis fabae, Rhopalosiphum padi., Macrosiphum pisi, Macrosiphum solanifolii, Cryptomyzus korschelti, Sapaphis mali, Hyalopterus arundinis* and *Myzus cerasi,* and bugs such as *Piesma quadratum, Dysdercus intermedius, Cimex lectularius, Rhodnius prolixus* and *Triatoma infestans.*

The most important of the biting insects are Lepidoptera such as *Plutella maculipennis, Lymantria dispar.,*

*Euproctis chrysorrhoea* and *Malacosoma neustria,* further *Mamestra brassicae, Agrotis segetum, Pieris brassicae, Hyponomeuta padella, Ephestia kuhniella* and *Galleria mellonella.*

Other representatives of biting insects are beetles (Coleoptera) such as *Sitophilus granarius, Leptinotarsa decemlineata, Dermestes frischi, Tribolium castaneum, Calandra* or *Sitophilus zeamais, Stegobium paniceum, Tenebrio molitor,* including soil-borne species such as wireworms (*Agriotes spec.*) and cockhafers (*Melolontha melolontha*); cockroaches such as *Blatella germanica, Periplaneta americana, Blatta orientalis, Blaberus giganteus, Blaberus fuscus,* and *Henschoutedenia flexivitta;* Orthoptera, e.g., *Acheta domestica,* termites such as *Reticulitermes flavipes,* and Hymenoptera such as ants, e.g., *Lasius niger.*

The Diptera essentially encompass flies such as *Drosophila melanogaster, Ceratitis capitata, Musca domestica, Fannia canicularis, Phormia regina, Calliphora erythrocephala* and *Stomoxys calcitrans;* mosquitoes such as *Aedes aegypti, Culex pipiens* and *Anopheles stephensi.*

Of the mites (Acari) particular importance attaches to spider mites (Tetranychidae) such as *Tetranychus telarius* (= *Tetranychus althaeae* or *Tetranychus urticae*) and *Paratetranychus pilosus* (= *Panonychus ulmi*); gall mites, e.g., Eriophyes ribis, and Tarsonemidae, e.g., *Hemitarsonemus latus* and *Tarsonemus pallidus;* and finally ticks such as *Ornithodorus moubata.*

The following examples demonstrate the biological action. The experiments were carried out with active ingredients listed in the foregoing table; the prior art active ingredient O,O-diethyl-O-[3,5,6-trichloropyridyl-(2)]-thiophosphate was used for comparison purposes.

EXAMPLE 1

Action on caterpillars of the cabbage moth (Plutella maculipennis)

Leaves of young cabbage plants are dipped for 3 seconds in aqueous emulsions of the active ingredients and, after having briefly allowed excess liquid to drip off, are placed on a moist filter paper in a Petri dish. 10 caterpillars of the 4th larval stage are then placed on each leaf. The action is assessed after 48 hours.

Results: mortality in %

| Concentration of emulsion | | 0.2% | 0.1% | 0.05% | 0.02% | 0.01% |
|---|---|---|---|---|---|---|
| Compound no. | 1 | 100 | 100 | 100 | 100 | 80 |
| | 2 | 100 | 50 | | | |
| | 4 | 100 | 100 | 100 | 80 | |
| | 3 | 100 | 100 | 80 | | |
| | 21 | 100 | 100 | 30 | | |
| | 20 | 100 | 100 | 100 | 20 | |

EXAMPLE 2

Contact action on ticks (*Ornithodorus moubata*)

Larvae of the tick *Ornithodurus moubata* in tea bags are dipped for 5 seconds in emulsions of various concentrations; the bags are then suspended. The mortality rate is determined after 48 hours.

Results: mortality in %

| Concentration of emulsion | | 0.1% | 0.05% | 0.02% | 0.01% |
|---|---|---|---|---|---|
| Compound no. | 1 | 100 | 100 | 100 | 80 |
| | 4 | 80 | | | |
| | 20 | 100 | 20 | | |
| | 16 | 100 | 100 | 30 | |

EXAMPLE 3

Contact action on houseflies (*Musca domestica*); continuous contact with treated glass plates Roughened glass plates having a side length of 15×15 cm are uniformly treated with acetonic solutions of the active ingredients. After the solvent has evaporated, 10 4-day old houseflies under a Petri dish (10 cm diameter) are placed on each plate. The mortality after 4 hours is taken as a guide.

The experiments are repeated at intervals until the treated plates are no longer effective.

The temperature at which the experiments are carried out is 20° to 22° C.

The mortality rate with 1 mg of active ingredient no. 1 was 100% after 20 days, compared with 80% after 7 days in the case of 1 mg of the prior art comparison compound.

We claim:

1. A pyridylphosphoric acid of the formula

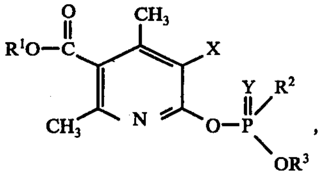

where X denotes hydrogen or halogen, Y denotes oxygen or sulfur, $R^1$ denotes linear or branched alkyl, alkenyl or alkynyl of a maximum of 6 carbon atoms, or unsubstituted or halogen-substituted phenyl or benzyl, $R^2$ denotes linear or branched alkyl, unsubstituted phenyl, substituted phenyl, alkyloxy or alkylthio of a maximum of 6 carbon atoms, alkenyloxy or alkenylthio of a maximum of 6 carbon atoms, alkynyloxy or alkynylthio of a maximum of 6 carbon atoms, amino or alkylamino with from 1 to 4 carbon atoms in the alkyl moiety, or dialkylamino with from 1 to 4 carbon atoms per alkyl moiety, and $R^3$ denotes alkyl of from 1 to 4 carbon atoms.

2. O,O-diethyl-O-[4,6-dimethyl-5-carboxyethylpyridin-(2)-yl]-thiophosphate.

3. O,O-diethyl-O-[4,6-dimethyl-5-carboxymethylpyridin-(2)-yl]-thiophosphate.

4. O,O-diethyl-O-[4,6-dimethyl-5-carboxybenzylpyridin-(2)-yl]-thiophosphate.

5. O-ethyl-S-n-propyl-O-[4,6-dimethyl-S-carboxyethylpyridin-(2)-yl]-dithiophosphate.

6. A pesticidal composition comprising an inert diluent, adjuvant or carrier and, as the active pesticidal ingredient, from 0.1 to 95% by weight of a pyridylphosphoric acid of the formula

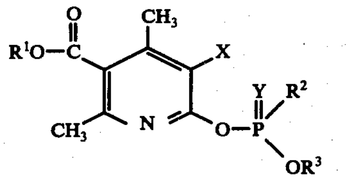

where X denotes hydrogen or halogen, Y denotes oxygen or sulfur, $R^1$ denotes linear or branched alkyl, alkenyl or alkynyl of a maximum of 6 carbon atoms, or unsubstituted or halogen-substituted phenyl or benzyl, $R^2$ denotes linear or branched alkyl, unsubstituted phenyl, substituted phenyl, alkyloxy or alkylthio of a maximum of 6 carbon atoms, alkenyloxy or alkenylthio of a maximum of 6 carbon atoms, alkynyloxy or alkynylthio of a maximum of 6 carbon atoms, amino or alkylamino with from 1 to 4 carbon atoms in the alkyl moiety, or dialkylamino with from 1 to 4 carbon atoms per alkyl moiety, and $R^3$ denotes alkyl of from 1 to 4 carbon atoms.

* * * * *